United States Patent
Khurram et al.

(10) Patent No.: US 9,708,235 B2
(45) Date of Patent: Jul. 18, 2017

(54) RECYCLING GAS TO HEAT THE HYDRODESULPHURIZATION SECTION

(71) Applicant: SAUDI BASIC INDUSTRIES CORPORATION, Riyadh (SA)

(72) Inventors: Shezada Khurram, Riyadh (SA); Ali Essa Al-Hammad, Riyadh (SA)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

(21) Appl. No.: 14/787,316

(22) PCT Filed: May 6, 2014

(86) PCT No.: PCT/IB2014/061244
§ 371 (c)(1),
(2) Date: Oct. 28, 2015

(87) PCT Pub. No.: WO2014/181256
PCT Pub. Date: Nov. 13, 2014

(65) Prior Publication Data
US 2016/0107963 A1 Apr. 21, 2016

Related U.S. Application Data

(60) Provisional application No. 61/819,714, filed on May 6, 2013.

(51) Int. Cl.
*C01B 3/38* (2006.01)
*C01B 3/34* (2006.01)
(Continued)

(52) U.S. Cl.
CPC ............ *C07C 29/1518* (2013.01); *C01B 3/34* (2013.01); *C01B 3/38* (2013.01); *C10L 3/10* (2013.01);
(Continued)

(58) Field of Classification Search
CPC .... C01B 2203/0233; C01B 2203/0883; C01B 2203/1241; C01B 2203/061; C01B 2203/045; C01B 2203/0475; C07C 31/04
(Continued)

(56) References Cited

U.S. PATENT DOCUMENTS 2,789,085 A * 4/1957 Rollman ................. C10B 55/04
201/17
4,181,503 A 1/1980 Lesieur et al.
(Continued)

FOREIGN PATENT DOCUMENTS

| EP | 2716597 A1 | 4/2014 |
| WO | 9965097 | 12/1999 |
| WO | 03063282 A1 | 7/2003 |

OTHER PUBLICATIONS

International Search Report for International Application No. PCT/IB2014/061244; International Filing Date: May 6, 2014; Date of Mailing: Sep. 1, 2014; 5 Pages.
(Continued)

*Primary Examiner* — Jafar Parsa

(74) *Attorney, Agent, or Firm* — Cantor Colburn LLP

(57) ABSTRACT

In one aspect, the present invention provides a method for recycling natural gas during a reformer startup in a methanol plant. The method comprises recycling natural gas from a point before entry into the natural gas saturator where the natural gas is recycled until the natural gas reaches a desired temperature.

15 Claims, 2 Drawing Sheets

(51) Int. Cl.
   *C07C 29/151* (2006.01)
   *C10L 3/10* (2006.01)
(52) U.S. Cl.
   CPC ............... *C10L 3/103* (2013.01); *C10L 3/106* (2013.01); *C01B 2203/1241* (2013.01); *C01B 2203/148* (2013.01); *C01B 2203/1604* (2013.01); *C10L 2290/06* (2013.01); *C10L 2290/10* (2013.01); *C10L 2290/60* (2013.01)
(58) Field of Classification Search
   USPC .......................................... 252/373; 518/700
   See application file for complete search history.

(56) References Cited

U.S. PATENT DOCUMENTS

| | | | | |
|---|---|---|---|---|
| 5,324,452 | A * | 6/1994 | Allam | B01J 19/0013 |
| | | | | 165/166 |
| 2004/0006916 | A1 | 1/2004 | Bruck et al. | |
| 2005/0209347 | A1* | 9/2005 | Bowe | B01J 19/249 |
| | | | | 518/703 |
| 2013/0090505 | A1* | 4/2013 | Catchpole | C10L 3/08 |
| | | | | 585/310 |
| 2014/0072888 | A1 | 3/2014 | Harada et al. | |

OTHER PUBLICATIONS

Written Opinion of the International Searching Authority for International Application No. PCT/IB2014/061244; International Filing Date: May 6, 2014; Date of Mailing: Sep. 1, 2014; 6 Pages.

* cited by examiner

RECYCLING GAS TO HEAT THE HYDRODESULPHURIZATION SECTION

CROSS REFERENCE TO RELATED APPLICATIONS

This application is a 371 of International Application No. PCT/IB2014/061244, filed May 6, 2014, which claims priority to U.S. Patent Application No. 61/819,714, filed May 6, 2013, which are incorporated herein by reference in their entirety.

BACKGROUND

Normal methanol plant start-up requires nine hours to fourteen hours to heat the hydrodesulphurization section to an optimum temperature to activate the dehydrosulfurization catalyst before feeding natural gas to the saturator for further processing. Since natural gas is being used for heating and is also concurrently being vented to flare, the existing start up process wastes substantial amounts of natural gas which has negative impact on the environment and also reduces the overall efficiency of the plant.

Accordingly, what is needed is a process which efficiently recycles natural gas instead of venting the natural gas to the flare system. Recycling of natural gas until the hydrodesulphurization section reaches the required temperature increases overall plant efficiency, enhances production, saves significant amounts of natural gas and reduces the carbon footprint of the plant.

SUMMARY

In accordance with the purposes of the invention, as embodied and broadly described herein, the invention, satisfies these and other needs. In one aspect, a method is provided comprising:

recycling natural gas during a reformer startup in a methanol plant, wherein the natural gas is recycled from a point before entry into a natural gas saturator, wherein the natural gas is recycled until the natural gas is heated to a desired temperature.

In another aspect, a method is provided for recycling natural gas during a steam reformer startup in a methanol plant comprising:

a) suctioning natural gas by a suction drum;

b) boosting natural gas by a natural gas booster downstream of the suction drum;

c) heating a steam reformer to heat a reformer feed gas downstream of the natural gas booster;

d) heating a hydrogenerator downstream of the steam reformer;

e) heating a sulfur adsorber downstream of the hydrogenerator;

f) recycling natural gas by a recirculation line downstream of the sulfur adsorber and upstream of the reformer;

g) cooling the recycled natural gas by a heat exchanger downstream of the sulfur adsorber;

h) suctioning the cooled recycled natural gas into the suction drum downstream of the heat exchanger;

wherein the natural gas is recycled until the reformer feed gas reaches a desired temperature.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
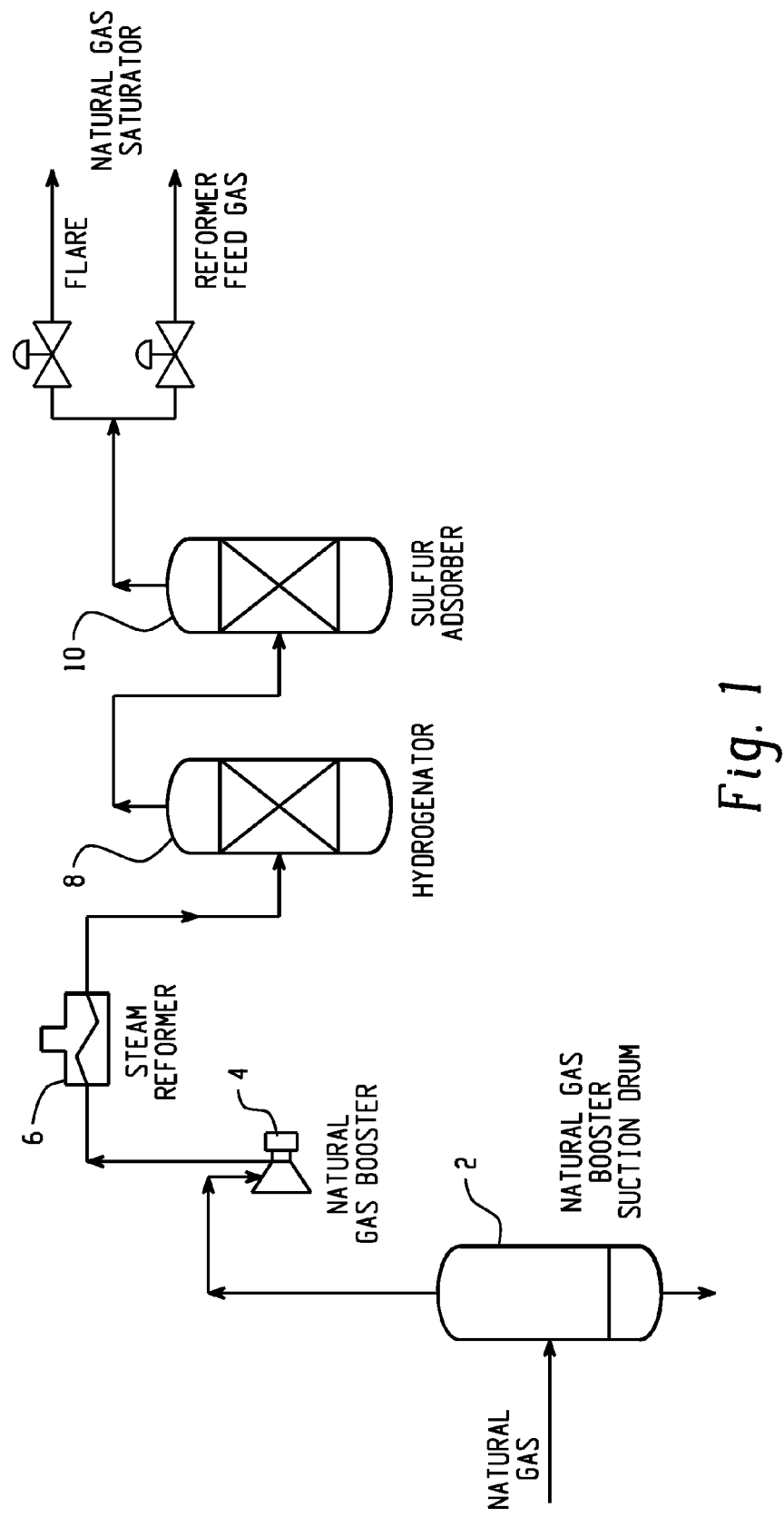
FIG. 1 illustrates the conventional process for reformer startup in a methanol plant.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Example included therein.

Before the present articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, examples of methods and materials are now described.

DEFINITIONS

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. Thus, if there are a variety of additional steps that can be performed it is understood that each of these additional steps can be performed with any specific embodiment or combination of embodiments of the methods of the invention.

Method

Previously at startup, both the reformer temperature and the flue gases temperature are low. The PNG isn't hot enough to heat this natural gas, to a temperature sufficient to activate the catalyst, at startup the natural gas would be sent to flare.

In some aspects, the present process described herein is a method for recycling natural gas during a reformer startup in a methanol plant. The method comprises recycling natural gas during a reformer startup where the natural gas is recycled from a point before entry into the natural gas saturator and where the natural gas is recycled until the natural gas reaches a desired temperature (e.g., a temperature of greater than or equal to 350° C., specifically, greater than or equal to 380° C.). In a further aspect, the natural gas is recycled from a point after passing through the preheater of the steam reformer (natural gas preheater ("PNG") which is part of the steam reformer). This recycle based start-up can be accomplished, for example, in around 7 to 10 hours. Essentially, a different heating medium (e.g., another source of natural gas (start-up natural gas)) is used to raise the temperature of the steam reformer to operating temperature. Meanwhile, the natural gas introduced into the system, is recycled until the desired temperature has been attained (e.g., greater than or equal to 350° C.)

Recycling of natural gas until the hydrodesulphurization section reaches the required temperature can increase overall plant efficiency, enhance production, save significant amounts of natural gas and reduces the carbon footprint of the plant.

In one aspect, the natural gas acts as a feedstock for the methanol plant. As used herein, feedstock is a term used to indicate a raw material. In another aspect, the natural gas heats the reformer in the methanol plant. In a further aspect, the natural gas can heat a steam reformer. At the start of the methanol plant, the natural gas can be sent to each unit of operation to get the desired temperature for the hydrodesulphurization section (HDS). In one aspect, the desired temperature is based on the temperature at which the HDS catalyst is activated.

In one aspect, the natural gas heats the hydrogenator and sulfur adsorber. In another aspect, the natural gas obtains the heat from the reformer convection section preheater (PNG). In a further aspect, the reformer is heated to the desired temperature with another source of natural gas. In an even further aspect, the natural gas enters the reformer convection section preheater (PNG) to be heated. In a yet further aspect, the natural gas passes repeatedly though the HDS section as the temperature gradually rises in the HDS section. In another aspect, the gradually rising temperature activates the HDS catalyst.

In one aspect, the desired temperature of the natural gas can be greater than or equal to 350° C. (e.g., 350° C. to 380° C.), including exemplary values 353° C., 355° C., 358° C., 360° C., 363° C., 365° C., 368° C., 370° C., 373° C., and 375° C. In further aspects, the temperature can be in a range derived from any two exemplary values. For example, the desired temperature of the natural gas ranges from 355° C. to 380° C., or 365° C. to 380° C. It is noted that the temperature of the natural gas can be measured after the steam reformer (e.g., between the steam reformer and the hydrogenator).

In one aspect, the method further comprises the step of cooling the recycled natural gas. In another aspect, the cooling comprises passing the recycled natural gas through a heat exchanger. In still another aspect, the recycled natural gas is cooled to the desired inlet compressor temperature.

In a further aspect, the recycled natural gas comprises methane, ethane, ethylene, or hydrogen or a combination thereof.

In still another aspect, the desired inlet compressor temperature ranges from 20° C. to 60° C. In a further aspect, the temperature can be in a range derived from any two exemplary values. For example, the desired inlet compressor temperature ranges from 22° C. to 60° C. Further for example, the desired inlet compressor temperature ranges from 35° C. to 45° C. In a further aspect, desired inlet compressor temperature is 40° C. In an even further aspect, the desired inlet compressor temperature depends on the booster suction requirement. Accordingly, the desired inlet compressor temperature can be any temperature appropriate to meet the temperature requirements for the booster suction drum.

In one aspect, the method does not comprise a natural gas flare step. In another aspect, the method does not comprise a flare to dispose of the excess natural gas. In a further aspect, the method does not comprise burning natural gas to dispose of the natural gas. In a further aspect, the method does not comprise a natural gas flare step during reformer start up. As used herein, flare, also known as a gas flare or flare stack, is a gas combustion device used to burn a combustible gas. In one aspect, the method does not comprise a natural gas flare step when recycling of the natural gas. In another aspect, the method can comprise a natural gas flare step in the methanol plant outside of recycling the natural gas. In a further aspect, the method can comprise a natural gas flare step in the methanol plant outside of the reformer startup.

Avoiding the use of a flare can be desirable to reduce thermal radiation, pollution, and acoustic impact. Further, avoiding the use of a flare can reduce emissions of carbon dioxide, methane, and other volatile organic compounds, for example sulfur compounds. In another aspect, avoiding the use of a flare can reduce hazards to human health by reducing toxins, which can cause asthma or other respiratory problems.

In another aspect, the method does not comprise a partial oxidation step. In a further aspect, the method does not comprise a full oxidation step or a partial oxidation step. In an even further aspect, the method does not comprise an oxidation step. In a yet further aspect, the method does not comprise an oxidation step because the method comprises recycling natural gas. In another aspect, the method does not comprise a reaction because the method comprises recycling natural gas.

In another aspect, the method does not comprise a partial oxidation step during the reformer start up. In a further aspect, the method does not comprise a full oxidation step or a partial oxidation step during the reformer start up. In an even further aspect, the method does not comprise an oxidation step during the reformer start up. In a yet further aspect, the method does not comprise an oxidation step because the method comprises recycling natural gas during the reformer start up. In another aspect, the method does not comprise a reaction because the method comprises recycling natural gas during the reformer start up.

In one aspect, the recycled natural gas consists essentially of natural gas. In another aspect, the recycled natural gas consists of natural gas. In a further aspect, only the natural gas is recycled. In still another aspect, the recycled natural gas does not comprise carbon monoxide or carbon dioxide, or a combination thereof. In a further aspect, the recycled natural gas comprises methane, ethane, ethylene, and hydrogen. In a yet further aspect, the recycled natural gas consists essentially of methane, ethane, ethylene, and hydrogen. In an even further aspect, the recycled natural gas comprises methane, ethane, and ethylene. In another aspect, the recycled natural gas consists essentially of methane, ethane, and ethylene. In still another aspect, the method does not comprise recycling syn gas, also called synthesis gas.

In one aspect, the recycled natural gas passes through a hydrodesulphurization section. In a further aspect, the recycled natural gas passes through the hydrodesulphurization section comprising a hydrogenerator and sulfur adsorber. In another aspect, the natural gas is recycled from a point after the exit from a hydrodesulphurization section. In a further aspect, the natural gas is recycled from a point after the exit from the sulfur absorber. In an even further aspect, the method comprises recirculating all of the natural gas.

In one aspect, the method comprises substantially no natural gas entering the natural gas saturator until it reaches the desired temperature. In still another aspect, the method does not comprise recycling a slip stream of natural gas. In another aspect, the desired temperature of the natural gas ranges from 350° C. to 380° C. In further aspects, the temperature can be in a range derived from any two exemplary values. For example, the desired temperature of the natural gas ranges from 355° C. to 380° C., or 355° C. to 375° C.

In one aspect, the recycled natural gas is recycled back to the suction drum. In a further aspect, the recycled natural gas is recycled back to the natural gas booster. In an even further aspect, the recycled natural gas is recycled back to the natural gas booster in a way that keeps the pressure constant. In still another aspect, the recycled natural gas heats a hydrodesulphurization section to activate a hydrodesulphurization catalyst. In a further aspect, the recycled natural gas is recycled back to a point before entry into the natural gas saturator. In a yet further aspect, the recycled gas is recycled back to a point upstream of the natural gas booster.

In some other aspects, a method for recycling natural gas during a steam reformer startup in a methanol plant is provided. The method comprises suctioning natural gas by a suction drum, boosting natural gas by a natural gas booster downstream of the suction drum, heating a steam reformer to heat a reformer feed gas downstream of the natural gas booster, heating a hydrogenerator downstream of the steam reformer, heating a sulfur adsorber downstream of the hydrogenerator, recycling natural gas by a recirculation line downstream of the sulfur adsorber and upstream of the reformer, cooling the recycled natural gas by a heat exchanger downstream of the sulfur adsorber, and suctioning the cooled recycled natural gas into the suction drum downstream of the heat exchanger where the natural gas is recycled until the reformer feed gas reaches a desired temperature. In some aspects, the desired temperature of the natural gas ranges from 350° C. to 380° C. In further aspects, the temperature can be in a range derived from any two exemplary values. For example, the desired temperature of the natural gas ranges from 355° C. to 380° C., or 360° C. to 380° C. Once the desired natural gas temperature is attained, the natural gas is no longer recycled, it is instead directed to the natural gas saturator.

In another aspect, the natural gas booster can have a pressure in an amount ranging from 2500 kPa to 2600 kPa, including exemplary values of 2510 kPa, 2520 kPa, 2530 kPa, 2540 kPa, 2550 kPa, 2560 kPa, 2570 kPa, 2580 kPa, and 2590 kPa. In further aspects, the pressure can be in a range derived from any two exemplary values. For example, the natural gas booster can have a pressure in an amount ranging 2510 kPa to 2590 kPa.

Referring now to FIG. 1, a typical existing process for reformer startup of a methanol plant is illustrated. Here, beginning at the left of FIG. 1, natural gas enters the suction drum 2 which removes water and/or any liquid vapors from the natural gas. Natural gas is directed to natural gas booster 4, which increases the pressure for downstream processes and then flows through steam reformer 6, which heats the natural gas. Natural gas then passes through hydrogenator 8 which desulfurizes an organic sulfur compound in the natural gas to provide hydrogen sulfide mixed with natural gas. Natural gas then flows through the sulfur adsorber 10 which, when the hydrodesulphurization catalyst is activated, removes hydrogen sulfide from natural gas. In the typical existing startup process, natural gas is then vented through the flare at the right hand side of FIG. 1.

During startup, natural gas heats the hydrodesulfurization section comprising both the hydrogenerator 8 and sulfur adsorber 10. Natural gas functions to heat hydrodesulfurization section 8 and 10 to a temperature which activates a hydrodesulfurization catalyst present in this section. At the beginning of methanol plant startup, the natural gas temperature can be too low to activate the hydrodesulfurization catalyst so large amounts of natural gas must be used to gradually heat the hydrodesulfurization section 8 and 10 to the required temperature for catalyst activation. Under operating conditions, natural gas is purified by the hydrodesulfurization section 8 and 10 before being fed to the reforming section for conversion to syn gas and eventually for conversion to methanol. Like parts are labeled with the same number between FIGS. 1 and 2.

Figure 2:
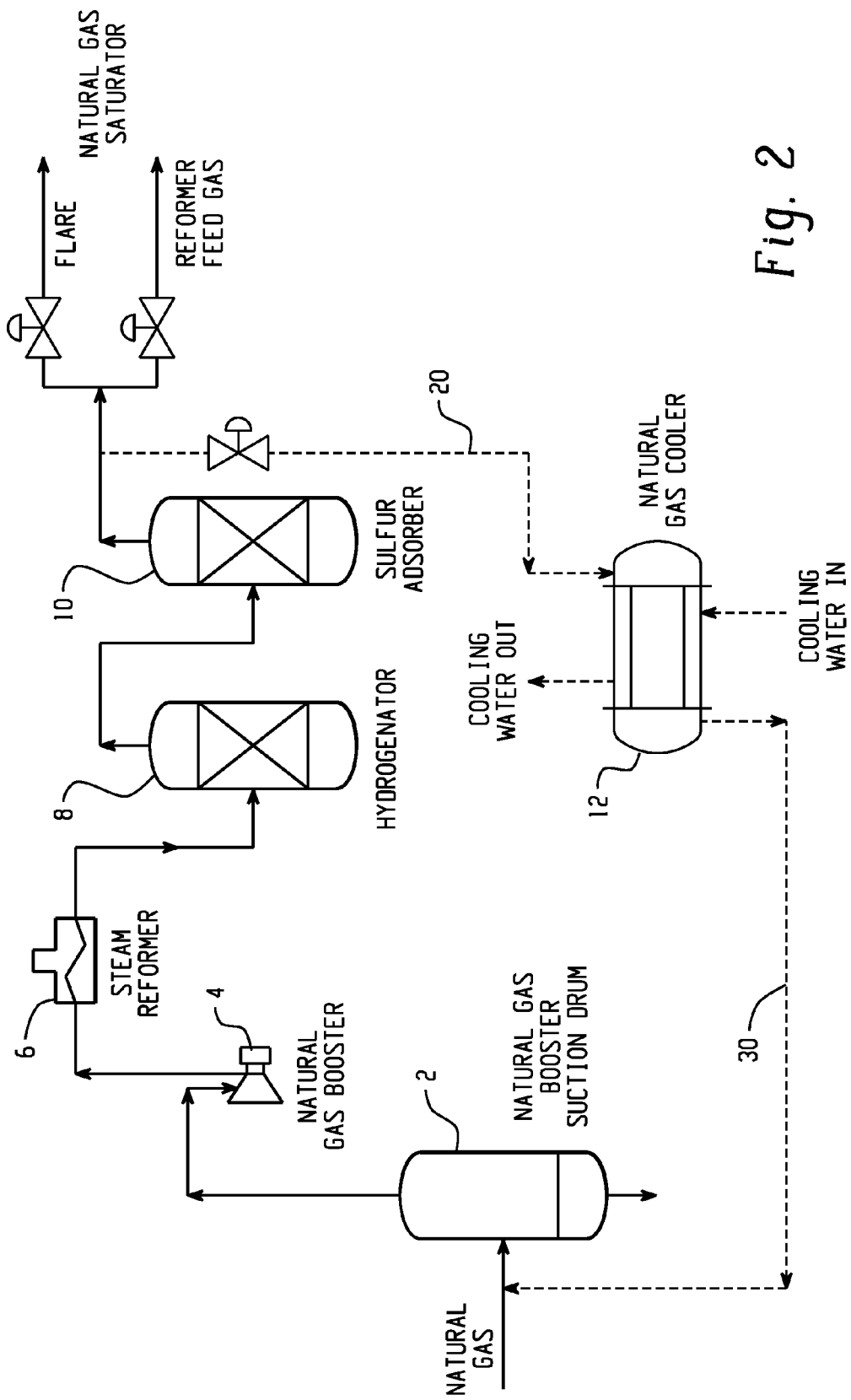
FIG. 2 illustrates a version of the inventive process described herein.

FIG. 2 illustrates one aspect of the present invention. Here, beginning at the left side of FIG. 2, natural gas enters the suction drum 2 which removes water and/or any liquid vapors from the natural gas. Generally, the temperature of the natural gas ranges from ranges from 20° C. to 60° C. Natural gas is directed to natural gas booster 4 which increases the pressure for downstream processes and then flows through steam reformer 6 which heats the natural gas. In one aspect, the natural gas is heated using the reformer conventional section. Natural gas then passes through the hydrogenerator 8, which, when activated by heating to the desired temperature, desulfurizes an organic sulfur compound to provide hydrogen sulfide mixed with natural gas. Natural gas is then passed through the sulfur adsorber 10, which when activated, removes hydrogen sulfide from natural gas. During startup, the natural gas heats the hydrogenerator 8 and the hydrodesulfurization section 10. Natural gas heats the hydrogenerator 8 and the hydrodesulfurization section 10 to a temperature which activates the hydrodesulfurization catalyst during startup. In another aspect, the desired temperature of the hydrogenerator 8 and the hydrodesulfurization section 10 ranges from 350° C. to 380° C. In the process depicted in FIG. 2, natural gas is not vented to the flare but is instead directed by recirculation via recycle line 20 to natural gas cooler 12 from a point after the sulfur adsorber and before the natural gas saturator. At the natural gas cooler 12, the natural gas is cooled to a temperature ranging from 20° C. to 60° C. In one aspect, the temperature of the natural gas is cooled to 40° C. at the natural gas cooler 12. After cooling, natural gas flows to the suction drum 2 via recycle line 30 to re-traverse the steps recited above. In another aspect, the recycle loop comprises recycle line 20, the natural gas cooler 12, and recycle line 30. In a further aspect, the recycle loop comprises recycle line 20 and recycle line 30. In a yet further aspect, the recycle loop comprises recycle line 20 connected to recycle line 30. The recycling process continues until the hydrogenerator 8 and hydrodesulfurization section 10 have reached a temperature ranging from 350° C. to 380° C. Natural gas is not sent to the flare vent but instead is recycled until the catalyst in the hydrodesulfurization section is activated.

After the desired temperature is reached and the HDS catalyst is activated, the natural gas can feed into the HDS reactor to remove the sulfur by preheating from the reformer to produce a clean natural gas. The clean natural gas can feed into the reforming section to be converted to syn gas, also called synthesis gas. As used herein, syn gas comprises hydrogen and carbon monoxide. After the conversion to syn gas, the syn gas can proceed to the methanol synthesis section for methanol production. In one aspect, the natural gas is the feed for the methanol process. However, during start-up, the natural gas temperature can be too low for catalyst activation and can be recycled to reach the desired temperature. In a further aspect, once the natural gas reaches the desired temperature, the natural gas becomes the feed for the methanol process. In other words, the natural gas is saturated with steam to produce the syngas that can be introduced to a methanol reactor.

Aspects

The disclosed method includes at least the following aspects.

Aspect 1: A method comprising:

recycling natural gas during a reformer startup in a methanol plant, wherein the natural gas is recycled from a point before entry into a natural gas saturator, wherein the natural gas is recycled until the natural gas heated to a desired temperature.

Aspect 2: The method according to aspect 1, wherein the desired temperature of the natural gas ranges from 350° C. to 380° C.

Aspect 3: The method according to any of aspects 1-2, wherein the method further comprises the step of cooling the recycled natural gas.

Aspect 4: The method according to any of aspects 1-3, wherein the cooling comprises passing the recycled natural gas through a heat exchanger.

Aspect 5: The method according to any of aspects 1-4, wherein the recycled natural gas is cooled to the desired inlet compressor temperature.

Aspect 6: The method according to any of aspects 1-5, wherein the desired inlet compressor temperature ranges from 20° C. to 60° C.

Aspect 7: The method according to any of aspects 1-6, wherein the method does not comprise a natural gas flare step.

Aspect 8: The method according to any of aspects 1-7, wherein the method does not comprise a partial oxidation step.

Aspect 9: The method according to any of aspects 1-8, wherein the recycled natural gas consists essentially of natural gas.

Aspect 10: The method according to any of aspects 1-9, wherein the recycled natural gas comprises methane, ethane, ethylene, or hydrogen or a combination thereof.

Aspect 11: The method according to any of aspects 1-10, wherein the recycled natural gas consists of natural gas.

Aspect 12: The method according to any of aspects 1-11, wherein the recycled natural gas does not comprise carbon monoxide or carbon dioxide, or a combination thereof.

Aspect 13: The method according to any of aspects 1-12, wherein the recycled natural gas passes through a hydrodesulphurization section.

Aspect 14: The method according to any of aspects 1-13, wherein the natural gas is recycled from a point after the exit from a hydrodesulphurization section.

Aspect 15: The method according to any of aspects 1-14, wherein the natural gas is recycled from a point after the exit from the sulfur absorber.

Aspect 16: The method according to any of aspects 1-15, wherein the method comprises substantially no natural gas entering the natural gas saturator until it reaches the desired temperature.

Aspect 17: The method according to any of aspects 1-16, wherein the desired temperature of the natural gas ranges from 350° C. to 380° C.

Aspect 18: The method according to any of aspects 1-17, wherein the method does not comprise recycling a slip stream of natural gas.

Aspect 19: The method according to any of aspects 1-18, wherein the method comprises recirculating all of the natural gas.

Aspect 20: The method according to any of aspects 1-19, wherein the recycled natural gas is recycled back to a suction drum.

Aspect 21: The method according to any of aspects 1-20, wherein the recycled gas is recycled back to a point upstream of the natural gas booster.

Aspect 22: The method according to any of aspects 1-21, wherein the recycled natural gas is recycled back to a point before entry into the natural gas saturator.

Aspect 23: The method according to any of aspects 1-22, wherein the recycled natural gas heats a hydrodesulphurization section to activate a hydrodesulphurization catalyst.

Aspect 24: A method for recycling natural gas during a reformer startup in a methanol plant comprising: a) suctioning natural gas by a suction drum; b) boosting natural gas by a natural gas booster downstream of the suction drum; c) heating a steam reformer to heat a reformer feed gas downstream of the natural gas booster; d) heating a hydrogenerator downstream of the steam reformer; e) heating a sulfur adsorber downstream of the hydrogenerator; f) recycling natural gas by a recirculation line downstream of the sulfur adsorber and upstream of the reformer; g) cooling the recycled natural gas by a heat exchanger downstream of the sulfur adsorber; and h) suctioning the cooled recycled natural gas into the suction drum downstream of the heat exchanger; wherein the natural gas is recycled until the reformer feed gas reaches a desired temperature.

Aspect 25: The method according to aspect 24, wherein the desired temperature of the natural gas ranges from 350° C. to 380° C.

Aspect 26: The method according to any of aspects 1-25, comprising directing no natural gas to a flare.

Aspect 27: The method according to any of aspects 1-26, further comprising determining if the natural gas has been heated to the desired temperature by measuring a temperature of the natural gas after it passes through a steam reformer and before the natural gas is recycled.

Aspect 28: The method according to any of aspects 1-27, further comprising, after the natural gas has reached the desired temperature, directing the natural gas to the natural gas saturator to form saturated natural gas.

Aspect 29: The method according to aspect 28, further comprising forming syngas from the saturated natural gas, and forming methanol from the syngas.

EXPERIMENTAL

The following example is put forth so as to provide those of ordinary skill in the art with a complete disclosure and description of how the articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for.

Example 1

During a typical (non-recycle) startup, more than 40,000 kg/hr of natural gas is compressed by the booster compressor and is vented to flare after passing through a preheater (PNG), Hydro-generator and Sulfur absorber. In the process scheme of the invention herein, the natural gas goes through the same route but instead of venting to flare is recycled to the booster compressor. Before entering the compressor, the recycle natural gas passes through a heat exchanger in order to reduce the temperature of the natural gas from 380° C. (maximum) to 40° C. which is in range of suction temperature required the compressor. The process is evaluated by using plant data. Tables 1 and 2 summarize the results for recycling natural gas.

TABLE 1

| Natural gas (NG) feed composition | |
|---|---|
| Composition | NG VENT |
| Methane | 90-92.6 |
| Ethane | 6.0-6.4 |
| Ethylene | 0.1-0.2 |
| Carbon Monoxide | 0.0 |
| Carbon Dioxide | 0.0 |
| Hydrogen | 0.78-0.8 |

TABLE 2

| Final Results | | |
|---|---|---|
| Business Impact | Units | Results |
| Total NG Saved during startup | Kg/12 hr | 500,000-550,000 |
| $CO_2$ impact | MT/12 hr | 1,500-1,600 |

The results in Table 2 are calculated using Aspen Hysys-7.2 a chemical engineering tool. As shown above, the total natural gas saved is about 500,000-550,000 kg/12 hr and the $CO_2$ impact is about 1,500-1,600 MT/12 hr.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for recycling natural gas during a reformer startup in a methanol plant comprising:
   a) suctioning natural gas by a suction drum;
   b) boosting natural gas by a natural gas booster downstream of the suction drum;
   c) heating a steam reformer to heat a reformer feed gas downstream of the natural gas booster;
   d) heating a hydrogenerator downstream of the steam reformer;
   e) heating a sulfur adsorber downstream of the hydrogenerator;
   f) recycling natural gas by a recirculation line downstream of the sulfur adsorber and upstream of the reformer;
   g) cooling the recycled natural gas by a heat exchanger downstream of the sulfur adsorber; and
   h) suctioning the cooled recycled natural gas into the suction drum downstream of the heat exchanger;
   wherein the natural gas is recycled until the reformer feed gas reaches a desired temperature.

2. The method according to claim 1, wherein the desired temperature of the natural gas ranges from 350° C. to 380° C.

3. The method according to claim 1, comprising directing no natural gas to a flare.

4. The method according to claim 1, further comprising determining if the natural gas has been heated to the desired temperature by measuring a temperature of the natural gas after said natural gas passes through a steam reformer and before the natural gas is recycled.

5. The method according to claim 1, further comprising, after the natural gas has reached the desired temperature, directing the natural gas to the natural gas saturator to form saturated natural gas.

6. The method according to claim 5, further comprising forming syngas from the saturated natural gas, and forming methanol from the syngas.

7. The method according to claim 1, wherein the recycled natural gas is cooled to 20° C. to 60° C.

8. The method according to claim 1, wherein the method does not comprise at least one of the following: a natural gas flare step and a partial oxidation step.

9. The method according to claim 1, wherein the recycled natural gas consists essentially of natural gas.

10. The method according to claim 1, wherein the recycled natural gas comprises methane, ethane, ethylene, or hydrogen or a combination thereof.

11. The method according to claim 1, wherein the recycled natural gas consists of natural gas.

12. The method according to claim 1, wherein the recycled natural gas does not comprise carbon monoxide or carbon dioxide, or a combination thereof.

13. The method according to claim 1, wherein the method does not comprise recycling a slip stream of natural gas.

14. The method according to claim 1, wherein the recycled natural gas is recycled back to at least one of a suction drum, a point upstream of a natural gas booster, and a point before entry into the natural gas saturator.

15. The method according to claim 1 further comprising a step, wherein the recycled natural gas heats a hydrodesulphurization section to activate a hydrodesulphurization catalyst.

* * * * *